(12) United States Patent
Zhang et al.

(10) Patent No.: US 11,696,934 B2
(45) Date of Patent: Jul. 11, 2023

(54) EDIBLE BLENDED VEGETABLE OIL FOR REDUCING BLOOD LIPIDS AND CHOLESTEROL

(71) Applicant: Jiangnan University, Wuxi (CN)

(72) Inventors: Hui Zhang, Wuxi (CN); Gangcheng Wu, Wuxi (CN); Xiaojing Li, Wuxi (CN); Xiguang Qi, Wuxi (CN); Yun Zhu, Wuxi (CN); Qingzhe Jin, Wuxi (CN); Xingguo Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 17/211,841

(22) Filed: Mar. 25, 2021

(65) Prior Publication Data
US 2022/0062369 A1     Mar. 3, 2022

(30) Foreign Application Priority Data
Aug. 29, 2020   (CN) .......................... 202010890967.7

(51) Int. Cl.
| | | |
|---|---|---|
| A61K 36/889 | (2006.01) | |
| A23L 33/12 | (2016.01) | |
| A23L 33/11 | (2016.01) | |
| A23L 33/00 | (2016.01) | |
| A61P 3/06 | (2006.01) | |
| A23D 9/007 | (2006.01) | |
| A61K 31/01 | (2006.01) | |
| A61K 31/355 | (2006.01) | |
| A61K 31/575 | (2006.01) | |
| A61K 36/48 | (2006.01) | |
| A61K 36/55 | (2006.01) | |
| A61K 36/61 | (2006.01) | |
| A61K 36/63 | (2006.01) | |
| A61K 36/899 | (2006.01) | |

(52) U.S. Cl.
CPC ............ *A61K 36/889* (2013.01); *A23D 9/007* (2013.01); *A23L 33/11* (2016.08); *A23L 33/12* (2016.08); *A23L 33/40* (2016.08); *A61K 31/01* (2013.01); *A61K 31/355* (2013.01); *A61K 31/575* (2013.01); *A61K 36/48* (2013.01); *A61K 36/55* (2013.01); *A61K 36/61* (2013.01); *A61K 36/63* (2013.01); *A61K 36/899* (2013.01); *A61P 3/06* (2018.01); *A23V 2002/00* (2013.01)

(58) Field of Classification Search
None
See application file for complete search history.

(56) References Cited

PUBLICATIONS

CN110353056A (English translation from Google Patents). (Year: 2019).*
WO2020063653A1 (English translation from Google Patents). (Year: 2020).*

* cited by examiner

*Primary Examiner* — Michael Barker
(74) *Attorney, Agent, or Firm* — Idea Intellectual Limited; Margaret A. Burke; Sam T. Yip

(57) ABSTRACT

The present invention provides an edible blended vegetable oil for reducing blood lipids and cholesterol. The trace elements in the edible blended vegetable oil include 15-300 mg/kg of polyphenols, 290-1700 mg/kg of β-sitosterol, 260-1500 mg/kg of campesterol, 150-1000 mg/kg of stigmasterol, 140-600 mg/kg of squalene, 50-160 mg/kg of parkerol, 40-120 mg/kg of γ-tocotrienol. The prepared edible blended vegetable oil of the present invention can achieve the effect of reducing blood lipids and cholesterol through a synergistic effect within the trace elements and a reasonable ratio within fatty acids. It is suitable for people with different health needs and has a broad market prospect and application value.

5 Claims, No Drawings

EDIBLE BLENDED VEGETABLE OIL FOR REDUCING BLOOD LIPIDS AND CHOLESTEROL

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCES TO RELATED APPLICATIONS

This application claims priority from Chinese patent application number 202010890967.7 filed on Aug. 29, 2020; the disclosure of which is incorporated herein by reference in its entirety.

FIELD OF THE INVENTION

The present invention relates to the technical field of oil refining processing. More particularly, it relates to an edible blended vegetable oil for reducing blood lipids and cholesterol.

BACKGROUND OF THE INVENTION

Oil not only provides energy to the human body, but is also closely related to the health of the human body. The Chinese Nutrition Society published the "Dietary Reference Intakes (DRIs) for Chinese citizens" in 2013, which firstly proposed the intake range of saturated fatty acids and polyunsaturated fatty acids. It is recommended to increase the intake of monounsaturated fatty acids, provided that the intake of above two fatty acid is met. Furthermore, the DRIs published in 2013 added for the first time the content of "the effect of plant compounds on the human body", and it is recommended to increase the intake of plant compounds in the diet to achieve the purpose of interfering with nutritional problems such as chronic diseases of people in modern world.

The main components of vegetable oil include triglycerides and a small amount of fat concomitants (also known as trace elements). These trace elements are closely related to the health of the human body. A series of epidemiological investigations, scientific research and nutritional intervention have studied the close relationship between trace elements and the health of the human body. For example, in the mid-1990s, Dr. Walter Willett, a director of the department of nutrition at Harvard University, proposed a kind of Mediterranean diet that conforms to modern nutrition. Mediterranean diet is closely related to polyphenols in olive oil; in addition, two Danish medical scientists Bang and Dyerberg proposed an "Eskimo diet" structure that can reduce the risk of cardiovascular and cerebrovascular diseases, where the trace elements of fat-squalene plays an important role.

The relationship between edible oils and elevated blood lipids and cholesterol is not only closely related to fatty acid composition, but also affected by trace elements of oils. At present, most of the patents on edible blended vegetable oil focus on an aspect of fatty acid composition. For example, CN Patent Application No. 201610495301.5 discloses a blended oil and its preparation method thereof, but this method only considers the composition of saturated fatty acids, monounsaturated fatty acids and polyunsaturated fatty acids, ignoring the content and proportion of trace elements in vegetable oils. CN Patent Application No. CN201910027591.4 discloses an edible blended vegetable oil. Although this patent stipulates the fatty acid composition and the total amount of trace elements such as phytosterols, squalene, and polyphenols, it does not stipulate the types and distribution of trace elements. Further, the edible blended vegetable oil in the aforementioned patents does not have the effect of reducing blood lipids and cholesterol. Although CN Patent Application Publication No. 201410675897.8 discloses a blended vegetable oil that can lower blood lipids, it is only described from the perspective of fatty acids, and the influence of trace elements of fat in vegetable oils is ignored. Some scholars have also studied the effect of nutritional and blended rice bran oil in regulating blood lipids. However, the preliminary experiments showed that the effect of the blended oil based on rice bran oil in regulating blood lipids is not outstanding compared with other blended vegetable oils.

In summary, if edible oils with balanced types and distribution of trace elements of fats can be taken on permanent basis, the health risks caused by lipid will be greatly reduced. Therefore, how to develop an edible blended vegetable oil that can reduce blood lipids and cholesterol is very important, which also greatly meets the consumers' demands for healthy blended vegetable oils.

SUMMARY OF THE INVENTION

This section aims to summarize some aspects of the embodiments of the present invention and to briefly describe some preferred embodiments. The simplification or omission may be made in this section, the abstract of the specification, and the title to avoid obscuring the purpose of this section, the abstract of the specification, and the title. Such simplification or omission may not be used to limit the scope of the present invention.

The present invention is made in view of the technical problems as above-mentioned.

Therefore, as one aspect of the present invention, there is provided an edible blended vegetable oil for reducing blood lipids and cholesterol to overcome the technical hurdles in the conventional technologies.

The present invention has been made in view of the above-mentioned technical problems and provides an edible blended vegetable oil for reducing blood lipids and cholesterol. The trace elements in the edible blended vegetable oil comprise 15-300 mg/kg of polyphenols, 290-1700 mg/kg of β-sitosterol, 260-1500 mg/kg of campesterol, 150-1000 mg/kg of stigmasterol, 140-600 mg/kg of squalene, 50-160 mg/kg of parkeol, 40-120 mg/kg of γ-tocotrienol; and different fatty acids in the edible blended vegetable oil comprising the following with respect to mass percentage of total fatty acids: 2%-15% of saturated fatty acids, 10%-50% of unsaturated fatty acids, and 18%-70% of polyunsaturated fatty acids having 30%-80% of n-3 polyunsaturated fatty acids and 20%-50% of n-6 polyunsaturated fatty acids.

In one embodiment of the present invention, all the polyphenols, the β-sitosterol, the campesterol, the stigmasterol, the squalene, the parkeol and the γ-tocotrienol are non-exogenous additives.

In one embodiment of the present invention, the edible blended vegetable oil comprises olive oil, linseed oil, coconut oil, rice bran oil, tea tree oil, soybean oil, or a combination thereof.

In one embodiment of the present invention, the edible blended vegetable oil is accounted for the total mass of the edible vegetable oil, comprising 5%-30% of olive oil, 20-50% of linseed oil, 5%-10% of coconut oil, 10%-25% of rice bran oil, 5%-20% of tea tree oil and 5%-25% of soybean oil.

In one embodiment of the present invention, the saturated fatty acids derive from one or both of C12:0 fatty acid and C14:0 fatty acid.

In one embodiment of the present invention, the n-3 polyunsaturated fatty acids derive from one or more of linolenic acid, EPA, and DHA.

In one embodiment of the present invention, a total content of all sterols in the edible blended vegetable oil is not specified, but the following numerical ranges are limited: 290-1700 mg/kg of β-sitosterol, 260-1500 mg/kg of campesterol, 150-1000 mg/kg of stigmasterol, and 50-160 mg/kg of parkeol.

In one embodiment of the present invention, a total content of all sterols in the edible blended vegetable oil is not specified, but the following numerical ranges are limited: 1195.8 mg/kg of β-sitosterol, 563.5 mg/kg of campesterol, 374.7 mg/kg of stigmasterol, and 374.7 mg/kg of parkeol.

In one embodiment of the present invention, a total content of the tocotrienol is not specified, but γ-tocotrienol is provided in a range of 40-120 mg/kg.

In one embodiment of the present invention, a total content of the tocotrienol is not specified, but γ-tocotrienol is provided in a range of 66 mg/kg.

The present invention has the following advantages:

The present invention provides an edible blended vegetable oil, where the trace elements in the edible blended vegetable oil include 15-300 mg/kg of polyphenols, 290-1700 mg/kg of 0-sitosterol, 260-1500 mg/kg of campesterol, 150-1000 mg/kg of stigmasterol, 140-600 mg/kg of squalene, 50-160 mg/kg of parkeol, 40-120 mg/kg of γ-tocotrienol; and different fatty acids in the edible blended vegetable oil are accounted for the percentage of total fatty acid quality, comprising 2%-15% of saturated fatty acids, 10%-50% of unsaturated fatty acids, and 18%-70% of polyunsaturated fatty acids having 30%-80% of n-3 polyunsaturated fatty acids and 20%-50% of n-6 polyunsaturated fatty acids; and all the polyphenols, β-sitosterol, campesterol, stigmasterol, squalene, parkeol and γ-tocotrienol are non-exogenous additives. The prepared edible blended vegetable oil of the present invention can achieve the effect of reducing blood lipids and cholesterol through a synergistic effect within the trace elements and a reasonable ratio within fatty acids. It is suitable for people with different health needs and has a broad market prospect and application value.

DETAILED DESCRIPTION

The above described objectives, features and advantages of the present invention will become more apparent from the detailed description.

In the following description, a lot of specific details are explained therein in order to make a person skilled in the art fully understands the present invention. It should be understood that the specific embodiments are provided for an illustrative purpose only, and should not be interpreted in a limiting manner. Those skilled in the art will appreciate that the invention described herein is susceptible to variations and modifications other than those specifically described.

Furthermore, references in the specification to "one embodiment", "an embodiment", "an example embodiment", etc., indicate that the embodiment described can include a particular feature, structure, or characteristic. The term "in one embodiment" mentioned in different parts of the specification do not all refer to the same embodiment, nor refer to a separate or selective embodiment mutually exclusive with other embodiments.

In the present invention, high-quality edible vegetable oil is selected, and then each component is added to the mixing tank according to the proportion. The temperature is kept below 35° C., and the mixture is slowly and uniformly stirred for 20-40 minutes. Finally, filtering and canning are performed to obtain the edible blended vegetable oil.

The present invention uses a cell model to evaluate the blood lipid and cholesterol content of oil, and the specific method is as follows:

(1) Cell Culture Basic

HepG2 cells were seeded in a plate with a diameter of 60 mm, and each hole within the plate was seeded with $10^5$ cells. 5 mL of DMEM high glucose culture medium containing 10% Fetal Bovine Serum (FBS) and 1% secondary antibody were added into the plate and placed in an incubator for cultivation. After culturing for 48 hours, the culture medium was discarded, the cells were rinsed with PBS (1 mL), and 5 mL of new DMEM cell culture medium containing FBS and secondary antibody was added again, and then placed in an incubator for cultivation and observation. The cells were subcultured when a fusion rate of the cells on the culture plate reaches 80% or more.

(2) Subculturing Cells

A culture dish with a diameter of 60 mm was selected as an example to culture cells. First, the culture medium was removed from the culture dish, and 1 mL of PBS was added to rinse the cells, and then the waste liquid was discarded. Next, 1 mL of trypsin was added and digested for 2.5 to 3 minutes, and the digestion status of the cells were observed under a microscope. 1 mL of DMEM cell culture medium containing FBS and double antibodies was added to stop the digestion, and the culture medium was blown with a pipette to make the cells fall off the bottom of the culture dish and be dispersed in the culture medium. The cell-containing culture medium was collected and placed in a 15 mL sterile centrifuge tube, and the tube was centrifuged at 1200 r/min for 5 minutes, and then the supernatant was discarded. 1 mL of DMEM cell culture medium containing FBS and double antibodies was added to resuspend the cells by pipetting, and the number of cells were counted in a hemocytometer and reseeded in a cell culture dish for basic cell culture.

(3) Cell Cryopreservation and Thawing

After steps of rinsing, digesting, centrifuging, discarding the supernatant, etc., the cells ready for cryopreservation were collected, and 1 mL of DMEM cell culture medium containing FBS and double antibodies, 900 μL of FBS solution and 100 μL of DMSO were added and distributed evenly into 1 mL cryovials, ensuring that the number of cells per tube is between $10^6$ to $10^7$ cells/mL.

Before cell thawing, two culture dishes with a diameter of 100 mm were firstly added with 10 mL of DMEM cell culture medium containing bovine serum and double antibodies. The cryovials were quickly removed from the liquid nitrogen storage tank and placed in a water bath with a constant temperature of 37° C. for quick thawing, and the cells were transferred to the culture dishes containing culture medium, and then the culture dishes were place in an incubator for basic culture.

(4) Cell Viability Assay

A 96-well plate was used to determine the cell viability, in which each sample was tested in six parallel experiments. The cells were seeded in the 96-well plate with a cell density of $10^4$ cells/well. After being placed in an incubator for 24 hours, the DMEM culture medium containing FBS and double antibodies was discarded. 100 μL/well of PBS was added to rinse the cells and discarded. Next, 100 μL/well serum-free DMEM culture medium containing different concentrations of oil digestion products (50-500 μmol/L, calculated by the concentration of fatty acid, filtered through a 220 nm filter) was added. In the blank control group, only the serum-free DMEM culture medium was added and the cells were cultured for 24 hours, and then the culture medium was discarded afterwards. PBS was added to rinse the cells and then discarded. Next, serum-free DMEM culture medium containing 10% MTT solution (v/v, 5 mg/mL) was added. After culturing for 4 hours, the culture medium was discarded, and PBS was added to rinse the cells and discarded. DMSO (150 μL/well) was added to dissolve blue violet crystals, which was placed on a microplate shaker for shaking for 15 minutes, and its absorbance at 490 nm was measure.

Cell survival rate (%)=absorbance of sample group/
absorbance of blank control group×100.

(5) Studies on the Treatment of Cells with Oil Digestion Products $10^6$ cells/well of HepG2 cells were seeded in a 6-well plate, and 2.5 mL of DMEM culture medium containing FBS and double antibodies was added. After culturing for 24 hours, the DMEM culture medium containing FBS and double antibodies was discarded. 1 mL/well of PBS was added to rinse the cells and discarded. Next, 2.5 mL/well of serum-free DMEM culture medium containing different concentrations of oil digestion products (200 μmol/L or 500 μmol/L, calculated by the concentration of fatty acid) was added. In the blank control group, only serum-free DMEM culture medium was added and the cells were cultured for 24 hours.

(6) Determination of Relevant Indexes of Lipid Accumulation in Cells

After rinsing the partially processed cells in step (5) with PBS to remove the waste solution, 150 uL of RIPA lysate containing a protein protection agent PMSF (final concentration is 1 mM) was added to each well, and the cells were lysed for 30 minutes and transferred into a centrifuge tube. The cells were centrifuged at 10000 g for 5 minutes under 4° C., and then follow the manuals of BCA protein concentration determination kit, triglyceride (TG), cholesterol (TC), high-density lipoprotein (HDL-c) and low-density lipoprotein (LDL-c) assay kit for determination of intracellular lipid accumulation related indexes.

EXAMPLE

Example 1

150 kg of edible rice bran oil, 150 kg of edible tea tree oil, 100 kg of edible olive oil, 50 kg of edible coconut oil, 450 kg of edible linseed oil and 100 kg of edible soybean oil are used and added to a mixing tank. The temperature is kept below 35° C., and the mixture is slowly and uniformly stirred for 20-40 minutes. Finally, filtering and canning are performed to obtain 1000 kg of edible blended vegetable oil. Parts of the blended oil obtained in the present invention are processed through a silica gel column to obtain a blended oil sample (−);

Parts of the blended oil obtained by the present invention are additionally added with polyphenols and β-sitosterol to make the content exceed the limited range referred to in the present invention, thereby obtaining a blended oil sample (+).

The percentage of main fatty acids and the content of trace elements in different edible vegetable oils are shown in Table 1-1.

TABLE 1-1

Percentage of main fatty acids and the content of trace elements in different edible vegetable oils (mg/kg)

| | | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|---|
| Contents of main fatty acids (%) | C18:1 | 44.1 | 40.7 | 63.5 | 80.7 | 5.4 | 16.5 | 22.9 | 33.7 | 33.7 | 33.7 |
| | C18:2 | 14.6 | 38.9 | 18.0 | 4.3 | 0.8 | 16.0 | 55.5 | 21.8 | 21.8 | 21.8 |
| | C18:3 | 1.4 | 1.6 | 1.2 | 0.6 | ND | 60.3 | 6.0 | 28.2 | 28.2 | 28.2 |
| | C12:0 | ND | ND | ND | ND | 49.5 | ND | ND | 2.5 | 2.5 | 2.5 |
| | C14:0 | 1.01 | 0.17 | ND | ND | 20.9 | ND | ND | 1.1 | 1.1 | 1.1 |
| Contents of trace elements (mg/kg) | Polyphenols | ND | 15.5 | 24.3 | 325.6 | 8.5 | 12.5 | 10.3 | 45.8 | 3.6 | 432.6 |
| | β-sitosterol | 0 | 3959.2 | 903.9 | 984.0 | 544.4 | 544.2 | 958.8 | 1195.8 | 153.3 | 2313.1 |
| | Campesterol | 0 | 2887.2 | 224.7 | 50.9 | 102.2 | 102.2 | 405.5 | 563.5 | 98.5 | 563.5 |
| | Stigmasterol | 0 | 1313.5 | 425.5 | 9.6 | 161.4 | 161.4 | 321.9 | 374.7 | 25.4 | 374.7 |
| | Parkerol | 0 | 0 | 370.9 | 157.4 | 0 | 0 | 0 | 71.3 | 34.2 | 71.3 |
| | Squalene | 0 | 107.2 | 193.9 | 2729.3 | 0 | 103.7 | 0 | 369.9 | 57.9 | 369.9 |
| | γ-tocotrienol | 4.25 | 380.6 | 54.3 | 0 | 5.4 | 1.1 | 0 | 66 | 16.7 | 66 |

ND stands for not detected.

The effects of different edible vegetable oils on the lipid levels in HepG2 cells are shown in Table 1-2, in which lard was used as a control group.

TABLE 1-2

Effects of different edible vegetable oils on lipid levels in HepG2 cells

| | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|
| Contents of triglycerides (mmol/gpro) | 0.82 | 0.55 | 0.41 | 0.49 | 0.56 | 0.5 | 0.78 | 0.36 | 0.69 | 0.44 |
| Contents of total cholesterol (mmol/gpro) | 0.80 | 0.33 | 0.11 | 0.18 | 0.16 | 0.17 | 0.62 | 0.04 | 0.35 | 0.20 |
| Contents of HDL-cholesterol (mmol/gpro) | 0.16 | 0.23 | 0.20 | 0.24 | 0.25 | 0.17 | 0.17 | 0.32 | 0.18 | 0.25 |
| Contents of LDL-cholesterol (mmol/gpro) | 0.37 | 0.20 | 0.15 | 0.21 | 0.12 | 0.15 | 0.18 | 0.09 | 0.26 | 0.18 |

From the above table, other vegetable oils have a certain reduction in triglycerides, total cholesterol and low-density lipoprotein compared with lard, while having an increase content of high-density lipoprotein. However, a blended oil has a better effect on reducing blood lipids and cholesterol. The effects of the blended oil (−) and blended oil (+) beyond the limitation of the present invention are reduced.

Example 2

150 kg of edible rice bran oil, 200 kg of edible tea tree oil, 50 kg of edible olive oil, 50 kg of edible coconut oil, 400 kg of edible linseed oil and 150 kg of edible soybean oil are used and added to a mixing tank. The temperature is kept below 35° C., and the mixture is slowly and uniformly stirred for 20-40 minutes. Finally, filtering and canning are performed to obtain the edible blended vegetable oil.

Parts of the blended oil obtained in the present invention are processed through a silica gel column to obtain a blended oil sample (−); parts of the blended oil obtained by the present invention are additionally added with stigmasterol or campesterol to make the content exceed the limited range referred to in the present invention, thereby obtaining a blended oil sample (+).

The percentage of main fatty acids and the content of trace elements in different edible vegetable oils are shown in Table 2-1.

TABLE 2-1

Percentage of main fatty acids and the content of trace elements in different edible vegetable oils (mg/kg)

| | | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|---|
| Contents of main fatty acids (%) | C18:1 | 44.1 | 40.7 | 63.5 | 80.7 | 5.4 | 16.5 | 22.9 | 33.1 | 33.1 | 33.1 |
| | C18:2 | 14.6 | 38.9 | 18.0 | 4.3 | 0.8 | 16.0 | 55.5 | 24.4 | 24.4 | 24.4 |
| | C18:3 | 1.4 | 1.6 | 1.2 | 0.6 | ND | 60.3 | 6.0 | 25.5 | 25.5 | 25.5 |
| | C12:0 | ND | ND | ND | ND | 49.5 | ND | ND | 2.5 | 2.5 | 2.5 |
| | C14:0 | 1.01 | 0.17 | ND | ND | 20.9 | ND | ND | 1.0 | 1.0 | 1.1 |
| Contents of trace elements (mg/kg) | Polyphenols | ND | 15.5 | 24.3 | 325.6 | 8.5 | 12.5 | 10.3 | 30.6 | 2.4 | 30.6 |
| | β-sitosterol | 0 | 3959.2 | 903.9 | 984.0 | 544.4 | 544.2 | 958.8 | 1212.6 | 162.3 | 1212.6 |
| | Campesterol | 0 | 2887.2 | 224.7 | 50.9 | 102.2 | 102.2 | 405.5 | 587.4 | 101.4 | 1894.2 |
| | Stigmasterol | 0 | 1313.5 | 425.5 | 9.6 | 161.4 | 161.4 | 321.9 | 403.5 | 23.1 | 1324.1 |
| | Parkerol | 0 | 0 | 370.9 | 157.4 | 0 | 0 | 0 | 82.1 | 18.2 | 82.1 |
| | Squalene | 0 | 107.2 | 193.9 | 2729.3 | 0 | 103.7 | 0 | 237.9 | 45.1 | 237.9 |
| | γ-tocotrienol | 4.25 | 380.6 | 54.3 | 0 | 5.4 | 1.1 | 0 | 68.7 | 13.2 | 68.7 |

ND stands for not detected.

The effects of different edible vegetable oils on the lipid levels in HepG2 cells are shown in Table 2-2, in which lard was used as a control group.

TABLE 2-2

Effects of different edible vegetable oils on lipid levels in HepG2 cells

|  | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|
| Contents of triglycerides (mmol/gpro) | 0.82 | 0.55 | 0.41 | 0.49 | 0.56 | 0.5 | 0.78 | 0.31 | 0.71 | 0.38 |
| Contents of total cholesterol (mmol/gpro) | 0.80 | 0.33 | 0.11 | 0.18 | 0.16 | 0.17 | 0.62 | 0.05 | 0.38 | 0.13 |
| Contents of HDL-cholesterol (mmol/gpro) | 0.16 | 0.23 | 0.20 | 0.24 | 0.25 | 0.17 | 0.17 | 0.36 | 0.19 | 0.28 |
| Contents of LDL-cholesterol (mmol/gpro) | 0.37 | 0.20 | 0.15 | 0.21 | 0.12 | 0.15 | 0.18 | 0.08 | 0.22 | 0.12 |

From the above table, other vegetable oils have a certain reduction in triglycerides, total cholesterol and low-density lipoprotein compared with lard, while having an increase content of high-density lipoprotein. However, a blended oil has a better effect on reducing blood lipids and cholesterol. The effects of the blended oil (−) and blended oil (+) beyond the limitation of the present invention are reduced.

Example 3

100 kg of edible rice bran oil, 100 kg of edible tea tree oil, 100 kg of edible olive oil, 100 kg of edible coconut oil, 350 kg of edible linseed oil and 250 kg of edible soybean oil are used and added to a mixing tank. The temperature is kept below 35° C., and the mixture is slowly and uniformly stirred for 20-40 minutes. Finally, filtering and canning are performed to obtain the edible blended vegetable oil. Parts of the blended oil obtained in the present invention are processed through a silica gel column to obtain a blended oil sample (−);

Parts of the blended oil obtained by the present invention are additionally added with campesterol or β-sitosterol to make the content exceed the limited range referred to in the present invention, thereby obtaining a blended oil sample (+).

The percentage of main fatty acids and the content of trace elements in different edible vegetable oils are shown in Table 3-1.

TABLE 3-1

Percentage of main fatty acids and the content of trace elements in different edible vegetable oils (mg/kg)

|  |  | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|---|
| Contents of main fatty acids (%) | C18:1 | 44.1 | 40.7 | 63.5 | 80.7 | 5.4 | 16.5 | 22.9 | 30.5 | 30.5 | 30.5 |
|  | C18:2 | 14.6 | 38.9 | 18.0 | 4.3 | 0.8 | 16.0 | 55.5 | 25.7 | 25.7 | 25.7 |
|  | C18:3 | 1.4 | 1.6 | 1.2 | 0.6 | ND | 60.3 | 6.0 | 22.9 | 22.9 | 22.9 |
|  | C12:0 | ND | ND | ND | ND | 49.5 | ND | ND | 4.9 | 4.9 | 4.9 |
|  | C14:0 | 1.01 | 0.17 | ND | ND | 20.9 | ND | ND | 2.1 | 2.1 | 2.1 |
| Contents of trace elements (mg/kg) | Polyphenols | ND | 15.5 | 24.3 | 325.6 | 8.5 | 12.8 | 10.3 | 44.7 | 0.9 | 44.7 |
|  | β-sitosterol | 0 | 3959.2 | 903.9 | 984.0 | 544.4 | 544.2 | 998.8 | 1069.3 | 56.7 | 3569.2 |
|  | Campesterol | 0 | 2887.2 | 224.7 | 50.9 | 102.0 | 102.2 | 405.5 | 463.6 | 13.8 | 2876.4 |
|  | Stigmasterol | 0 | 1313.5 | 425.5 | 9.6 | 161.4 | 161.4 | 321.9 | 327.9 | 22.1 | 327.9 |
|  | Parkerol | 0 | 0 | 370.9 | 157.4 | 0 | 0 | 0 | 52.8 | 1.4 | 52.8 |
|  | Squalene | 0 | 107.2 | 193.9 | 2729.3 | 0 | 103.7 | 0 | 349.7 | 32.1 | 349.7 |
|  | γ-tocotrienol | 4.25 | 380.6 | 54.3 | 0 | 5.4 | 1.1 | 0 | 44.4 | 4.6 | 44.4 |

ND stands for not detected.

The effects of different edible vegetable oils on the lipid levels in HepG2 cells are shown in Table 3-2, in which lard was used as a control group.

TABLE 3-2

Effects of different edible vegetable oils on lipid levels in HepG2 cells

|  | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|
| Contents of triglycerides (mmol/gpro) | 0.82 | 0.55 | 0.41 | 0.49 | 0.56 | 0.5 | 0.78 | 0.26 | 0.89 | 0.22 |

TABLE 3-2-continued

Effects of different edible vegetable oils on lipid levels in HepG2 cells

| | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|
| Contents of total cholesterol (mmol/gpro) | 0.80 | 0.33 | 0.11 | 0.18 | 0.16 | 0.17 | 0.62 | 0.06 | 0.81 | 0.11 |
| Contents of HIDL-cholesterol (mmol/gpro) | 0.16 | 0.23 | 0.20 | 0.24 | 0.25 | 0.17 | 0.17 | 0.35 | 0.18 | 0.25 |
| Contents of LDL-cholesterol (mmol/gpro) | 0.37 | 0.20 | 0.15 | 0.21 | 0.12 | 0.15 | 0.18 | 0.09 | 0.29 | 0.14 |

From the above table, other vegetable oils have a certain reduction in triglycerides, total cholesterol and low-density lipoprotein compared with lard, while having an increase content of high-density lipoprotein. However, a blended oil has a better effect on reducing blood lipids and cholesterol. The effects of the blended oil (−) and blended oil (+) beyond the limitation of the present invention are reduced.

Example 4

200 kg of edible rice bran oil, 150 kg of edible tea tree oil, 250 kg of edible olive oil, 100 kg of edible coconut oil, 200 kg of edible linseed oil and 100 kg of edible soybean oil are used and added to a mixing tank. The temperature is kept below 35° C., and the mixture is slowly and uniformly stirred for 20-40 minutes. Finally, filtering and canning are performed to obtain the edible blended vegetable oil.

Parts of the blended oil obtained in the present invention are processed through a silica gel column to obtain a blended oil sample (−); parts of the blended oil obtained by the present invention are additionally added with polyphenols, campesterol or stigmasterol to make the content exceed the limited range referred to in the present invention, thereby obtaining a blended oil sample (+).

The percentage of main fatty acids and the content of trace elements in different edible vegetable oils are shown in Table 4-1.

TABLE 4-1

Percentage of main fatty acids and the content of trace elements in different edible vegetable oils (mg/kg)

| | | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|---|
| Contents of main fatty acids (%) | C18:1 | 44.1 | 40.7 | 63.5 | 80.7 | 5.4 | 16.5 | 22.9 | 43.9 | 43.9 | 43.9 |
| | C18:2 | 14.6 | 38.9 | 18.0 | 4.3 | 0.8 | 16.0 | 55.5 | 20.4 | 20.4 | 20.4 |
| | C18:3 | 1.4 | 1.6 | 1.2 | 0.6 | ND | 60.3 | 6.0 | 13.3 | 13.3 | 13.3 |
| | C12:0 | ND | ND | ND | ND | 49.5 | ND | ND | 4.9 | 4.9 | 4.9 |
| | C14:0 | 1.01 | 0.17 | ND | ND | 20.9 | ND | ND | 2.1 | 2.1 | 2.1 |
| Contents of trace elements (mg/kg) | Polyphenols | ND | 15.5 | 24.3 | 325.6 | 8.5 | 12.5 | 10.3 | 92.9 | 3.5 | 564.9 |
| | β-sitosterol | 0 | 3959.2 | 903.9 | 984.0 | 544.4 | 544.2 | 958.8 | 1432.6 | 99.8 | 1432.6 |
| | Campesterol | 0 | 2887.2 | 224.7 | 50.9 | 102.2 | 102.2 | 405.5 | 695.1 | 25.8 | 4687.8 |
| | Stigmasterol | 0 | 1313.5 | 425.5 | 9.6 | 161.4 | 161.4 | 321.9 | 409.6 | 14.9 | 3537.2 |
| | Parkerol | 0 | 0 | 370.9 | 157.4 | 0 | 0 | 0 | 95.0 | 3.8 | 95.0 |
| | Squalene | 0 | 107.2 | 193.9 | 2729.3 | 0 | 103.7 | 0 | 763.9 | 38.9 | 763.9 |
| | γ-tocotrienol | 4.25 | 380.6 | 54.3 | 0 | 5.4 | 1.1 | 0 | 85.03 | 13.2 | 85.03 |

ND stands for not detected.

The effects of different edible vegetable oils on the lipid levels in HepG2 cells are shown in Table 4-2, in which lard was used as a control group.

TABLE 4-2

Effects of different edible vegetable oils on lipid levels in HepG2 cells

| | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|
| Contents of triglycerides (mmol/gpro) | 0.82 | 0.55 | 0.41 | 0.49 | 0.56 | 0.5 | 0.78 | 0.26 | 0.77 | 0.34 |

TABLE 4-2-continued

Effects of different edible vegetable oils on lipid levels in HepG2 cells

| | Lard | Rice bran oil | Tea tree oil | Olive oil | Coconut oil | Linseed oil | Soybean oil | Blending oil | Blending oil (−) | Blending oil (+) |
|---|---|---|---|---|---|---|---|---|---|---|
| Contents of total cholesterol (mmol/gpro) | 0.80 | 0.33 | 0.11 | 0.18 | 0.16 | 0.17 | 0.62 | 0.02 | 0.85 | 0.09 |
| Contents of HIDL-cholesterol (mmol/gpro) | 0.16 | 0.23 | 0.20 | 0.24 | 0.25 | 0.17 | 0.17 | 0.42 | 0.12 | 0.35 |
| Contents of LDL-cholesterol (mmol/gpro) | 0.37 | 0.20 | 0.15 | 0.21 | 0.12 | 0.15 | 0.18 | 0.05 | 0.32 | 0.11 |

From the above table, other vegetable oils have a certain reduction in triglycerides, total cholesterol and low-density lipoprotein compared with lard, while having an increase content of high-density lipoprotein. However, a blended oil has a better effect on reducing blood lipids and cholesterol. The effects of the blended oil (−) and blended oil (+) beyond the limitation of the present invention are reduced.

The present invention provides an edible blended vegetable oil, which can achieve the effect of reducing blood lipids and cholesterol through a synergistic effect within the trace elements and a reasonable ratio within fatty acids. It is suitable for people with different health needs and has a broad market prospect and application value.

Though reference is made to preferred examples for detailed illustration of the present invention and non-limiting thereto, a skilled person in the art should understand that the technical solutions provided by the present invention can be changed or replaced by equivalents without departing from the spirit and scope of the technical solutions described herein, which should fall within the scope of the appended claims.

What is claimed is:

1. An edible blended vegetable oil for reducing blood lipids and cholesterol consisting essentially of 5 wt. %-30 wt. % olive oil, 20 wt. %-50 wt. % linseed oil, 5 wt. %-10 wt. % coconut oil, 10 wt. %-25 wt. % rice bran oil, 5 wt. %-20 wt. % tea tree oil and 5 wt. %-25 wt. % soybean oil, polyphenols, and β-sitosterol.

2. An edible blended vegetable oil for reducing blood lipids and cholesterol selected from the group consisting of:
   a) 15 wt. % edible rice bran oil, 15 wt. % edible tea tree oil, 10 wt. % edible olive oil, 5 kg edible coconut oil, 45 wt. % edible linseed oil, and 10 wt. % of edible soybean oil;
   b) 15 wt. % edible rice bran oil, 20 wt. % of edible tea tree oil, 5 wt. % of edible olive oil, 5 wt. % of edible coconut oil, 40 wt. % of edible linseed oil, and 15 wt. % of edible soybean oil;
   c) 10 wt. % edible rice bran oil, 10 wt. % edible tea tree oil, 10 wt. % edible olive oil, 10 wt. % edible coconut oil, 35 wt. % edible linseed oil, and 25 wt. % edible soybean oil; and
   d) 20 wt. % edible rice bran oil, 15 wt. % edible tea tree oil, 25 wt. % edible olive oil, 10 wt. % of edible coconut oil, 20 wt. % edible linseed oil, and 10 wt. % edible soybean oil.

3. A method for preparing an edible blended vegetable oil for reducing blood lipids and cholesterol comprising:

blending an oil composition of 5 wt. %-30 wt. % olive oil, 20 wt. %-50 wt. % linseed oil, 5 wt. %-10 wt. % coconut oil, 10 wt. %-25 wt. % rice bran oil, 5 wt. %-20 wt. % tea tree oil and 5 wt. %-25 wt. % soybean oil, to form a blended oil composition, the blended oil composition including:

30.6-92.9 mg/kg of polyphenols, 1069.3-1432.6 mg/kg of β-sitosterols, 405.5-695.1 mg/kg of campesterols, 327.9-409.6 mg/kg of stigmasterols, 52.8-95 mg/kg of parkeols, and 44.4-85.03 mg/kg of γ-tocotrienols;

2%-15% of a saturated fatty acid, 10%-50% of a monounsaturated fatty acid, and 18%-70% of a polyunsaturated fatty acid, the polyunsaturated fatty acid having 30%-80% of a n-3 polyunsaturated fatty acid and 20%-50% of a n-6 polyunsaturated fatty acid; and adding polyphenols and β-sitosterol to the blended oil composition.

4. The method of claim 3, wherein the saturated fatty acid further comprises one or both of C12:0 fatty acid and C14:0 fatty acid.

5. The method of claim 3, wherein the n-3 polyunsaturated fatty acid further comprises one or more of linolenic acid, EPA, and DHA.

* * * * *